United States Patent
Yarkoni et al.

(10) Patent No.: US 6,933,271 B2
(45) Date of Patent: Aug. 23, 2005

(54) CHIMERIC TOXINS FOR TARGETED THERAPY

(75) Inventors: Shai Yarkoni, Kfar Saba (IL); Amotz Nechushtan, Ramat Hasheron (IL); Haya Lorberboum-Galski, Jerusalem (IL); Irina Marianovsky, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/147,346
(22) PCT Filed: Jun. 4, 1997
(86) PCT No.: PCT/IL97/00180
§ 371 (c)(1), (2), (4) Date: Mar. 1, 1999
(87) PCT Pub. No.: WO97/46259
PCT Pub. Date: Dec. 11, 1997

(65) Prior Publication Data
US 2002/0028914 A1 Mar. 7, 2002

(30) Foreign Application Priority Data
Jun. 4, 1996 (IL) ................................................ 118570

(51) Int. Cl.$^7$ .............................................. A61K 38/00
(52) U.S. Cl. ............................ 514/2; 530/313; 530/350
(58) Field of Search ........................ 435/69.7; 530/300, 530/313, 350; 514/2; 536/23.1, 23.4, 24.1; 424/183.1

(56) References Cited

U.S. PATENT DOCUMENTS 5,378,688 A * 1/1995 Nett et al.

FOREIGN PATENT DOCUMENTS

| WO | 90 09799 | 9/1990 |
|----|----------|--------|
| WO | 93 15751 | 8/1993 |
| WO | 96 24675 | 8/1996 |
| WO | 97 22364 | 6/1997 |

OTHER PUBLICATIONS

Imai et al., Cancer 74:2555–61, 1994.*
Chaudhary et al., Nature 339:394–97, 1989.*

(Continued)

Primary Examiner—Larry R. Helms
(74) Attorney, Agent, or Firm—Browdy and Neimark, PLLC

(57) ABSTRACT

The present invention relates particularly to neoplastic cells targeted chimeric toxins comprising of cell targeting moieties and cell killing moieties for recognizing and for destroying the neoplastic cells, wherein the cell targeting moieties consist of gonadotropin releasing hormone homologues and the cell killing moieties consist of *Pseudomonas* Exotoxin A. The present invention further relates to pharmaceutical compositions containing as an active ingredient these neoplastic cells targeted chimeric toxins and to a method for the production of these chimeric toxins. The said invention also relates to a method for cancer therapy, treating malignant carcinoma cells and benign hyperplasia including uterine lyomyoma cells, extra uterian endometrial island cells, benign hyperplasia of prostate and breast and pituitary tumor adenoma cells, by the use of the above-mentioned chimeric toxins.

23 Claims, 8 Drawing Sheets

OTHER PUBLICATIONS

Chaudhary et al., Proc. Natl. Acad. Sci. USA 84:4538–4542, 1987.*
Chaudhary et al., The Journal of Biological Chemistry 265:16306–16310, 1990.*
Johnson et al., Cancer Treatment Reviews 2:1–31, 1975.*
Jian. Sci. Am. 271:58–65, 1994.*
Dermer. Biotechnology 12:320, 1994.*
Gura. Science 278:1041–1042, 1997.*
Chatterjee et al., Cancer Immunol. Immunother 38:75–82, 1994.*
Ahmi Ben–Yehudah, Diana Prus, and Haya Lorberboum–Galski; I.V. Administration of L–GNRH–PE66 Efficiently Inhibits Growth of Colon Adenocarcinoma Xenografts in Nude Mice; Int. J. Cancer: 92, 263–268 (2001).
Ahmi Ben–Yehudah, Shai Yarkoni, Amotz Nechushtan, Ruth Belostotsky and Haya Lorberbourn–Galski; Linker–Based GNRH–PE Chemeric Proteins Inhibit Cancer Growth in Nude Mice; Medical Oncology (1999), p. 16, 38–45.
Amotz Nechushtan, Shai Yarkoni, Irina Marianovsky, and Haya Lorberboum–Galski; Adenocarcinoma Cells are Targeted by the New GNRH–PE$_{66}$ Chimeric Toxin Through Specific Gonadotropin–Releasing Hormone Binding Sites; The Journal of Biological Chemistry, vol. 272, No. 17, Issue of Apr. 25, pp. 11597–11603, 1997.
(1) Nechushtan, Amotz et al., "Adenocarinoma cells are targeted by the new GnRH–PE66 chimeric toxin through specific gonadotropin–releasing hormone binding sites", J. Biol. Chem, (1997).
(2) Rusiecki, V. K. et al., "GnRH–toxin chimera as chemosterilants: Synthesis and conjugation of GnRH analogs to truncated bacterial toxins", Pept. 1994, Proc. Eur. Pept, Symp., 23rd (1995), Meeting Date 1994, pp. 765–766.

* cited by examiner

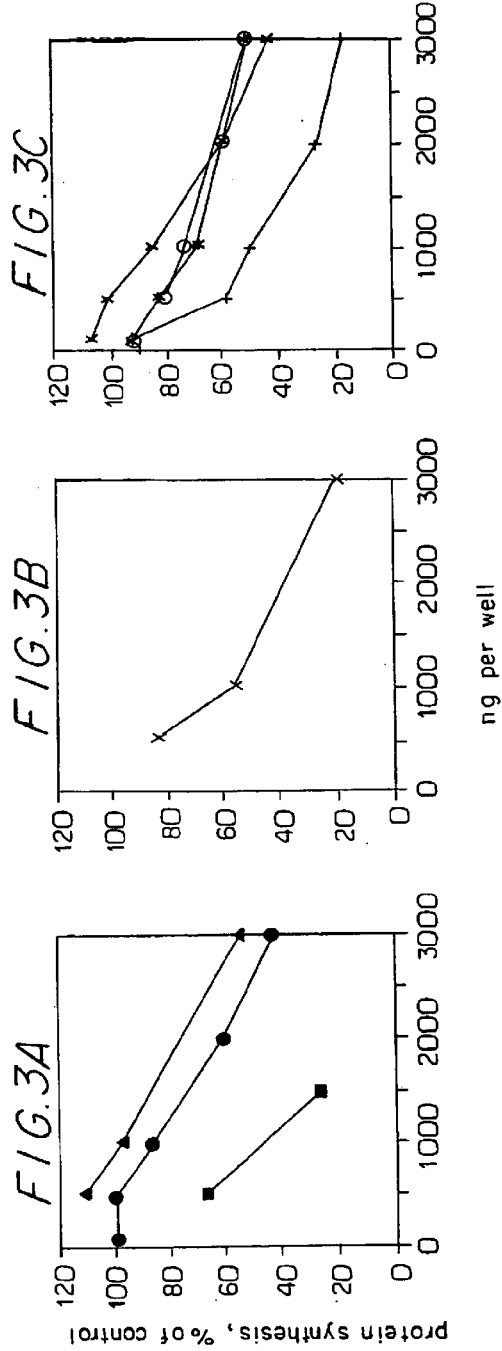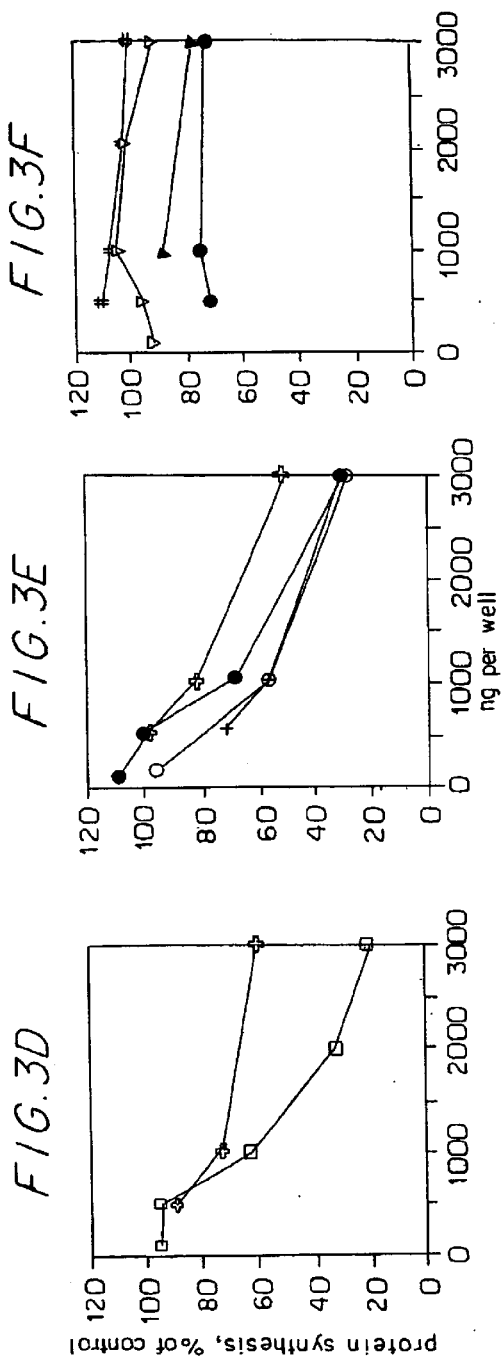

CHIMERIC TOXINS FOR TARGETED THERAPY

FIELD OF THE INVENTION

The present invention relates generally to therapeutic agents useful particularly in cancer targeted therapy but also in treating malignant adenocarcinomas, such as breast, colon, hepatic, ovarian and renal adenocarcinomas, and treating benign tumors of the uterus, hyperplasia, endometriosis, BPH, polycystic disease of the breast and pituitary adenomas.

More specifically, the said invention relates to *Pseudomonas* exotoxin based chimeric toxins aimed at those neoplastic cells bearing gonadotropin-releasing hormone binding sites. The present invention further relates to pharmaceutical compositions comprising as an active ingredient the above-mentioned neoplastic cell-targeting chimeric toxins. Furthermore, the present invention relates to a method for the production of said chimeric toxins. These chimeric proteins, according to the present invention, are comprised of cell-targeting moieties which consist of gonadotropin releasing hormone homologues linked to cell-killing moieties which consist, preferably, of the bacterial toxin *Pseudomonas* exotoxin A, for recognizing and destroying neoplastic cells bearing gonadotropin releasing hormone binding sites.

Targeting is a term for the selective delivery of chemotherapeutic agents to specific cell populations. It is possible to create chimeric molecules that possess cell-targeting and cellular toxin domains. These chimeric molecules function as cell selective poisons by virtue of their ability to target selective cells and then kill those cells via their toxin component. *Pseudomonas* exotoxin A (hereinafter called PE), a bacterial toxin used in construction of such chimeric proteins, acts by irreversibly arresting protein synthesis in eukaryotic cells, resulting in cell death.

The term "gonadotropin releasing hormone homologues" in this invention relates to the gonadotropin releasing hormone gene itself or its analogues and antagonists. Also included in the scope of the present invention are salts of the described chimeric proteins. The term "salts" includes both salts of carboxy groups as well as acid addition salts of amino groups of the protein molecule. The invention further relates to pharmaceutical compositions comprising the chimeric proteins as defined above together with a pharmaceutically acceptable inert carrier. The proteins of the present invention may be administered by methods known in the art for the administration of proteins.

BACKGROUND OF THE INVENTION

Gonadotropin releasing hormone (hereinafter called GnRH) participates in the hypothalamic-pituitary gonadal control of human reproduction. The involvement of GnRH has been demonstrated in several carcinomas and GnRH analogue treatment has been applied in breast, prostatic, pancreatic, endometrial and ovarian cancers (Kadar et al. *Prostate* 12:229–307, 1988). These analogues suppress tumor cell growth in vitro and in vivo. The existence of GnRH binding sites was revealed in the corresponding malignant cells and in well-established cell lines (Emons et al. *J. Clin. Endocrinol. Metab.* 77:1458–1464, 1993), though preliminary results suggest that the GnRH receptor involved may differ from the previously documented receptor (Kakar et al. *Biochem. Biophys. Res. Comm.* 189:289–295, 1992).

Although GnRH binding sites have been demonstrated in a number of solid tumors and various carcinoma cell lines derived mainly from hormone dependent tissues, their existence in colon or renal carcinoma has not been previously documented. The presence of specific GnRH binding sites in colon, breast, prostate, ovarian endometrium, renal and liver carcinomas, is shown here. Surprisingly, the specific GnRH binding sites are not limited to hormone-dependant tissues, as indicated by the marked killing of colon adenocarcinoma, renal cell adenocarcinoma and hepatocarcinoma cells.

WO93/15751 describes various conjugates of GnRH, a linking group and *Pseudomonas* exotoxin A, prepared using the techniques of synthetic organic chemistry, used for the sterilization of animals by killing gonadotropin releasing cells of the animals pituitary gland.

The present invention describes the construction, by the techniques of genetic engineering, of PE based chimeric toxins, aimed at targeting those neoplastic cells bearing GnRH binding sites. The chimeric toxins of the present invention are fusion proteins and, as such, do not contain a chemical linking group (as in the above-mentioned patent). Therefore, they are completely different proteins from the molecules described in WO93/15751.

Using different kinds of targeting moieties, a large number of immunotoxins have been generated in the last 20 years by chemical linkage techniques or recombinant DNA technology. The size of these targeting moieties varies widely, ranging from large antibodies to small growth factors, cytokines and antibody fragments.

The ability of large chimeric proteins, as the Met-GnRH-PE constructions described in the present invention, to target cells via a very small portion of the polypeptide (a peptide of ten amino acids, as used as the targeting moiety of the present invention), and yet retain their original functions, namely binding and internalization, open up new possibilities in designing targeted immunotoxins.

Colon, breast, and prostate cancer—three out of the four major malignancies occurring in humans, together with ovarian, endometrium, renal and liver carcinomas, account for more than 50% of cancer related death. The presence of specific GnRH binding sites in all of these cancers, may suggest a more general role of GnRH and/or GnRH-like peptides in the malignant process.

Collectively, these results disclose what could be considered the Achilles' heel of these malignant growths, a finding that could open up new vistas in the fight against cancer.

In view of their efficient growth inhibition of the above-mentioned cancer cells and their specificity regarding the non-target cells, the novel Met-GnRH-PE chimeric toxins are promising candidates for cancer treatment.

SUMMARY OF THE INVENTION

The present invention relates particularly to neoplastic cell-targeting chimeric toxins comprising cell-targeting moieties and cell-killing moieties for recognizing and for destroying the neoplastic cells, wherein the cell-targeting moieties consist of gonadotropin releasing hormone homologues and the cell-killing moieties consist of *Pseudomonas* exotoxin A. The present invention further relates to pharmaceutical compositions containing as an active ingredient these neoplastic cell-targeting chimeric toxins and to a method for the production of these chimeric toxins. The said invention also relates to a method for cancer therapy, treating malignant adenocarcinoma and hepatocarcinoma cells and benign hyperplasia including uterine leiomyoma cells, extrauterine endometrial island cells, benign hyperplasia of prostate and breast, and pituitary tumor adenoma cells, by the use of the above-mentioned chimeric toxins.

DETAILED DESCRIPTION OF THE INVENTION

The present invention describes *Pseudomonas* exotoxin A (PE) based chimeric toxins constructed by ligating an oligonucleotide encoding ten amino acids of a gonadotropin releasing hormone (GnRH) analog (GnRH coding sequence with tryptophan replacing glycine as the sixth amino acid), and a preceding Met (see FIG. 1C), upstream of a mutated form of PE (domains I (muted), II and III ) thereby generating Met-GnRH-PE66, and a ten amino acid synthetic GnRH oligomer (GnRH coding sequence with tryptophan replacing glycine as the sixth amino acid), with a preceding Met, ligated to domains II and III of the PE, thereby generating Met-GnRH-PE40 protein.

The applications, potential markets and commercial advantages of the said chimeric proteins according to the present invention are listed:

There are two main applications:

1) Malignant Adenocarcinomas and Hepatocarcinomas:

Breast, colon, ovarian and renal adenocarcinomas and hepatocarcinoma were all sensitive to Met-GnRH-PE mediated cytotoxicity. Thus, the potential market for this new chimeric protein includes all adenocarcinoma and hepatocarcinoma patients, either as a first line of treatment or for patients in which other modalities of treatment had failed.

2) Benign Tumors of the Uterus and Hyperplasia:

This group of pathologies includes various tissues that are known to be sensitive to GnRH and thus can be targeted by the Met-GnRH-PE chimeric proteins.

a. Uterine:

Uterine leiomyoma is the most common benign tumor in women. The uterine myomas are found to carry a large number of GnRH receptors. GnRH analogs are clinically used for down-regulation and shrinkage of these myomas. The disadvantage of GnRH analogs is that these compounds cannot be used for long periods and the myomas return to their original size after cessation of the treatment. The use of Met-GnRH-PE for the destruction of the myomas can help to avoid what was considered to be imminent hysterectomies.

b. Endometriosis—Endometrioma:

The existence of endometrial tissue out of the uterus leads to the disease called endometriosis which can cause infertility, abdominal pain and even surgical interventions. The endometrial islands are known to be very sensitive to hormonal changes. One of the therapeutic modalities found to be clinically efficient is the GnRH analog. Using Met-GnRH-PE, these explants of endometrial tissue can be eliminated, thereby helping infertile couples as well as women who are undergoing laparotomy for the resection of these endometrial islands. The treatment of both the leiomyoma and the endometria can be administered systematically or locally by either ultrasonic or laparoscopic guided injection into the peritoneal cavity.

c. Benign Prostatic Hyperplasia (BPH):

The prostatic cells are known to express GnRH receptors and prostatic cancer is successfully treated today with GnRH agonists. The BPH causes severe symptoms of dysuria, urinary retention and sometimes can be treated only by prostatectomy. The use of Met-GnRH-PE can therefore replace prostatectomy procedures carried out on prostate hyperplasia that is not malignant.

d. Polycystic Disease of the Breast:

The mammary cells are also known to express the GnRH receptors. As in the case of BPH, the polycystic disease of the breast may be symptomatic, cause pain and may mimic breast carcinoma. The use of Met-GnRH-PE may eliminate the need for numerous check-ups and needless mammograms and help woman suffering from breast pains and non-malignant breast tumors.

e. Pituitary Adenoma:

Some of the pituitary adenomas are derived from gonadotropic cells. The pituitary adenoma, even though non-malignant, can cause a grave prognosis by causing local pressure on vital organs (eyes, brain stem). The trans-sphenoidal surgery used for the pituitary adenoma has many disadvantages, including recurrency and neurological sequela. Met-GnRH-PE may be aimed directly against the gonadotropic cells without damaging other functions of the pituitary gland. Met-GnRH-PE chimeric toxin may be administered intrathecally.

Commercial Advantages:

1. The wide variety of tumors that respond to the Met-GnRH-PE chimeric protein.
2. The high selectivity that allows a large therapeutic range.
3. The use of GnRH as a targeting peptide leaving the large population of postmenopausal women in whom the GnRH has no physiological role perfect candidates for the treatment.
4. Its high specificity enables systemic administration together with the local effect.
5. The ability to eradicate small populations of cells in a tissue that will not itself be harmed.

The proteins of the present invention may be administered by methods known in the art for the administration of proteins. Also included in the scope of the present invention are salts of the described chimeric proteins. The term "salts" includes both salts of carboxy groups as well as acid addition salts of amino groups of the protein molecule. Salts of the carboxy group may be formed by methods known in the art and include both inorganic salts as well as salts with organic bases. The invention further relates to pharmaceutical compositions comprising the chimeric proteins as defined above together with a pharmaceutically acceptable inert carrier. The pharmaceutical composition may be administered by injection (intravenous, intra-articular, subcutaneous, intramuscular, intrathecal or intraperitoneal) topical application, oral administration, sustained release, or by any other route including the enteral route.

The said invention will be further described in detail by the following experiments and figures. These experiments and figures do not intend to limit the scope of the invention but to demonstrate and clarify it only.

DESCRIPTION OF THE FIGURES

FIG. 1A, SDS-PAGE gel and FIG. 1B', immunoblotting analysis of TGnRH-PE66 plasmid expression. Whole cell extract of the lysed bacteria (lane 1). Soluble fraction (lane 2). Insoluble fraction (lane 3). FIG. 1C, construction of TGnRH-PE66 plasmid.

▦ T7 promotor. ▢ GnRH analogue peptide. ⁝⁝ Ampicillin®. ▩ PE664Glu. The numbers represent the corresponding amino acids.

Figure 2A:
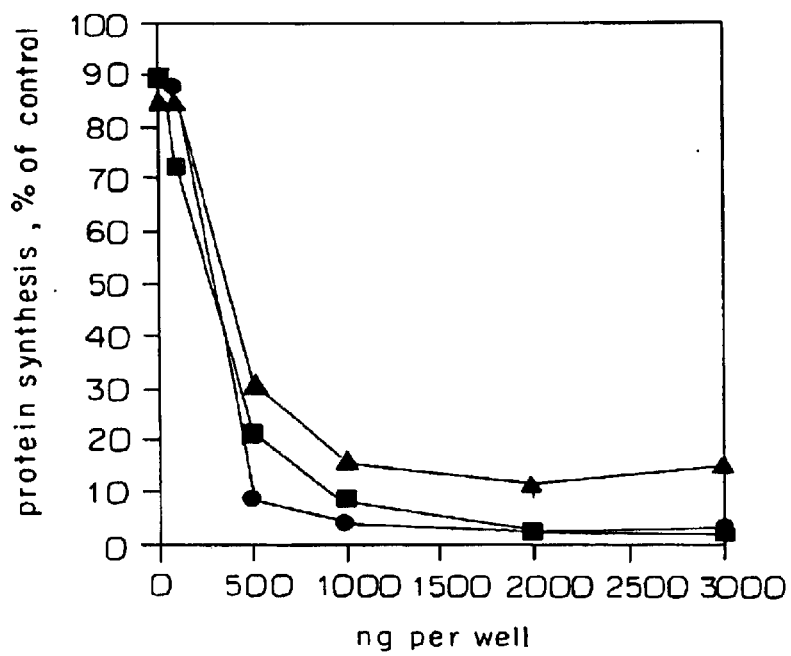
Figure 2B:
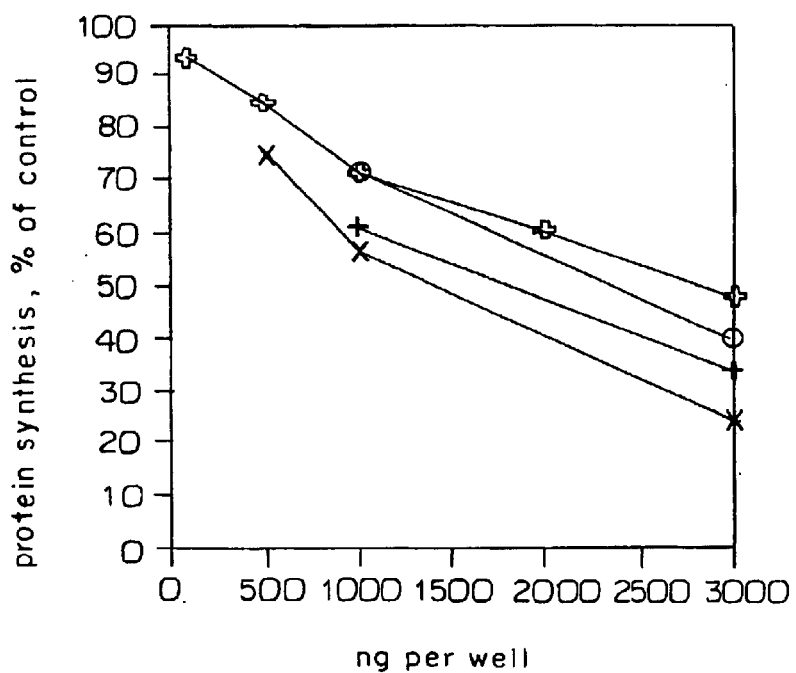

FIGS. 2A and 2B: The effect of increasing concentrations of Met-GnRH-PE66 on various cell lines.

FIG. 2A: ■ SW-48 colon adenocarcinoma, ● HepG2 hepatocarcinoma, ▲ Caco2 colon adenocarcinoma.

FIG. 2B: ✿ OVCAR3 ovarian adenocarcinoma, ✳ HeLa cervix adenocarcinoma, ○ MDA MB-231 breast adenocarcinoma, ✕ HT-29 colon adenocarcinoma.

FIGS. 3A–3F: The effect of Met-GnRH-PE66 on various primary cultures. FIG. 3A, colon carcinoma primary cultures established from three patients. FIG. 3B, renal cell carcinoma primary culture. FIG. 3C, breast carcinoma primary cultures established from four patients. FIG. 3D, ovarian carcinoma primary cultures established from two patients. FIG. 3E, metastases of primary cultures established from the corresponding patients represented in FIGS. 3A, 3C and 3D by the same symbols. FIG. 3F, control cells: # leukocytes. ▶ bone marrow. ● fibroblasts. ▽ colon.

Figure 4A:
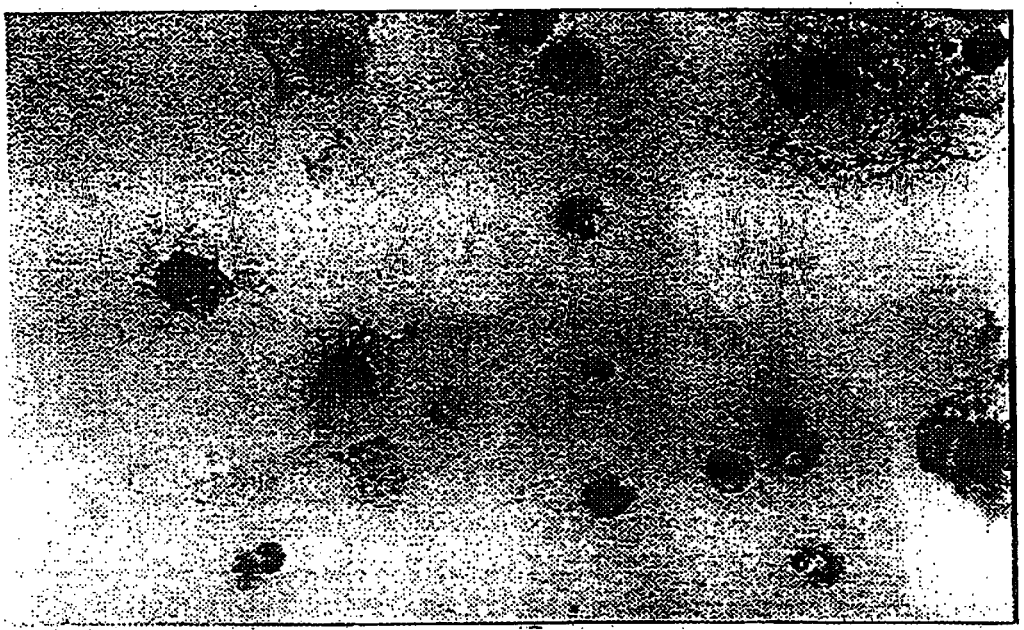
Figure 4B:

FIGS. 4A–4B: Histopathological diagnosis of primary cultures. FIG. 4A, anti-keratin positive staining of a colon primary culture. FIG. 4B, anti-desmin negative staining of a colon primary culture.

Figure 5:
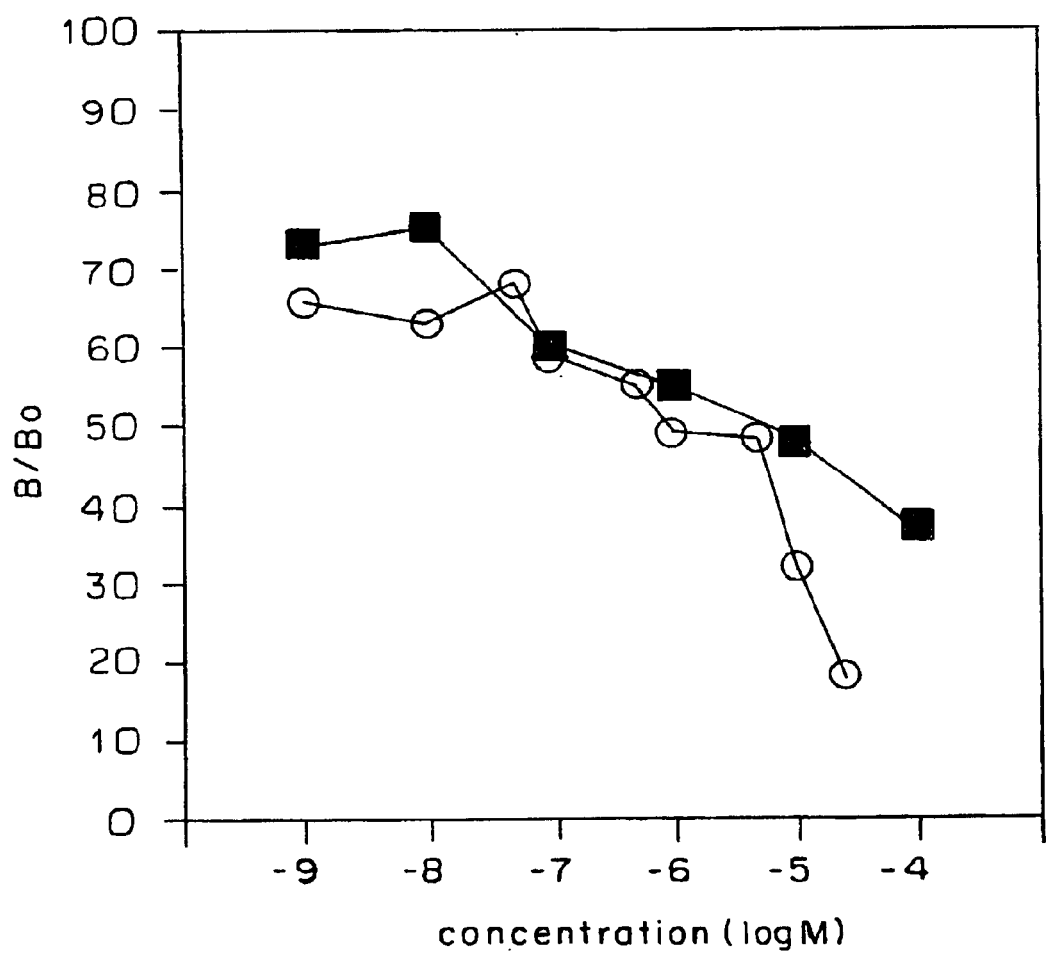

FIG. 5: Displacement of [$^{125}$I] GnRH bound to membranes of SW-48 cells by: ○ Met-GnRH-PE66. ■ GNRH analogue (des-Gly$^{10}$, [d-Ala$^6$]-LHRH).

Figure 6:
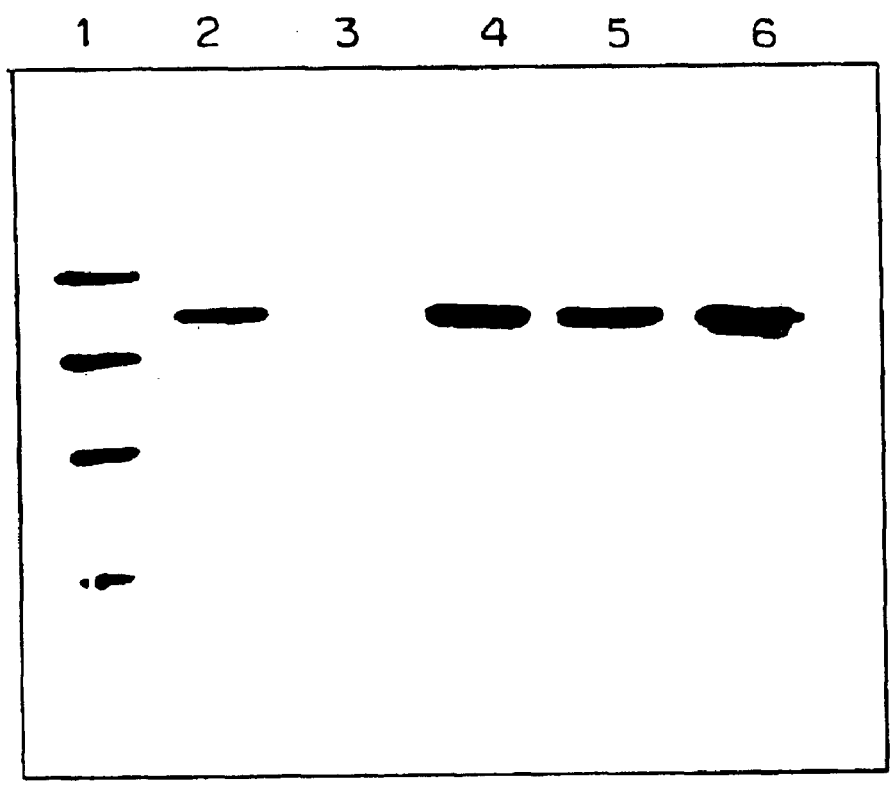

FIG. 6: Purification of Met-GnRH-PE66. Lane 1—protein marker. Lane 2—whole cell extract. Lane 3—soluble fraction. Lane 4—insoluble fraction after refolding. Lane 5—after DEAE-Sepharose column. Lane 6—after Sepharyl S-200 HR column.

Figure 7:
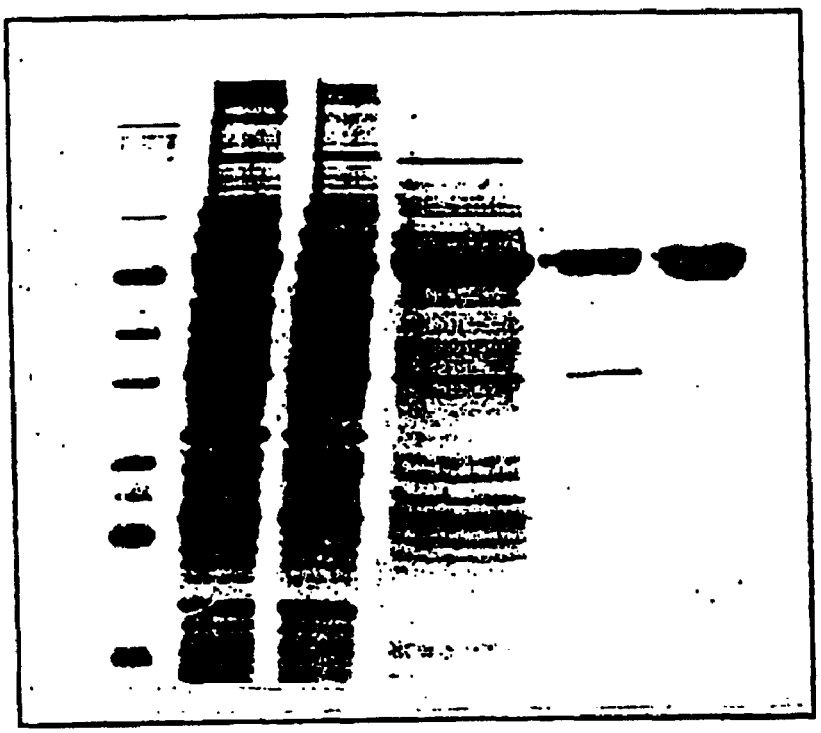

FIG. 7: Purification of Met-GnRH-PE40: Lane 1—protein marker. Lane 2—whole cell extract. Lane 3—soluble fraction. Lane 4—insoluble fraction after refolding. Lane 5—after DEAE-Sepharose column. Lane 6—after Sepharyl S-200 HR column.

Figure 8:
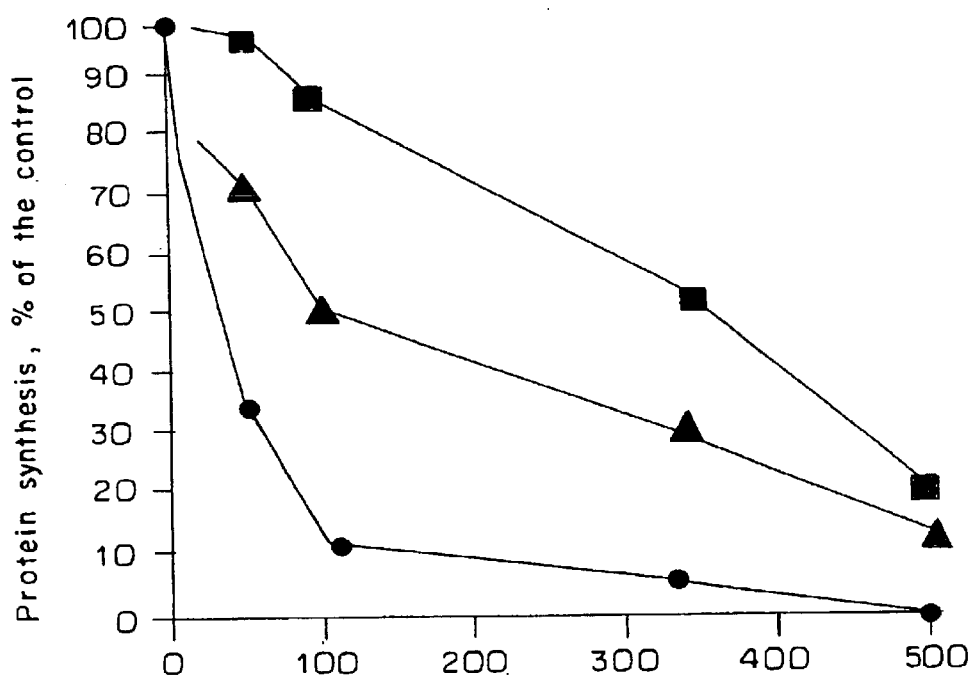

FIG. 8: Effects of Met-GnRH-PE chimeric proteins on SW-48 colon adenocarcinoma cell line:
- ■ Met-GnRH-PE66 insoluble fraction after refolding.
- ▲ Met-GnRH-PE66 purified protein.
- ● Met-GnRH-PE40 purified protein.

EXPERIMENTS

Experiment 1

Met-GnRH-PE66 Chimeric Toxin Construction

A plasmid vector carrying the mutated full length PE gene (pJY3A1136-1, 3) (Chaudhary et al., *J. Biol. Chem.* 256:16306–16310, 1990) was cut with NdeI and Hind III. The insert was a 36 base pair synthetic oligomer consisting of the GnRH coding sequence with tryptophan replacing glycine as the sixth amino acid, and was flanked by NdeI (5' end) and HindIII (3' End) restriction sites. The resulting TGnRH-PE66 plasmid was confirmed by restriction endonucleases digestion and DNA sequence analysis (FIG. 1C).

Experiment 2

TGnRH-PE40 Plasmid Construction

To construct the Met-GnRH-PE40 protein (Met-GnRH-domains II and III of the PE), the TGnRH-PE66 plasmid vector (FIG. 1C) was digested with NdeI and BamHI and ligated to a NdeI-BamHI 750 bp fragment from the plasmid PHL-906 (Fishman et al., *Biochemistry* 33:6235–6243, 1994) along with an insert which is a 36 base pair synthetic oligomer consisting of the GnRH coding sequence with tryptophan replacing glycine as the sixth amino acid, flanked by NdeI (5' end) and HindIII (31' end) restriction sites. The resulting TGnRH-PE40 plasmid was confirmed by restriction endonuclease digestion and DNA sequence analysis.

Experiment 3

Protein Expression

The protein expression method was the same for Met-GnRH-PE40 and Met-GnRH-PE66, unless mentioned. *Escherichia coli* strain BL21 (DE3) carrying the plasmid TGnRH-PE66 was grown in LB medium containing ampicillin (100 μg/ml) and *Escherichia coli* strain BL21 (DE3) carrying the plasmid GnRH-PE40 was grown in Super-LB medium containing ampicillin (50 μg/ml). After reaching an A600 value of 1.5–1.7, the cultures were induced 90 minutes for Met-GnRH-PE66 and overnight for Met-GnRH-PE40, at 37° C. with 1 mM isopropyl-d-thiogalactoside (IPTG). Cells were collected by centrifugation and the pellet was incubated at −70° C. for several hours.

The frozen pellet was thawed and suspended in lysis buffer (50 mM Tris HC1, pH 8.0, 1 mM EDTA and lysozyme 0.2 mg/ml), followed by sonication (3×30 seconds) and centrifugation at 35,000×g for 30 minutes. The supernatant (soluble fraction) was removed and the pellet (insoluble fraction) served as the source for the chimeric proteins and for their purification.

Figure 1A:
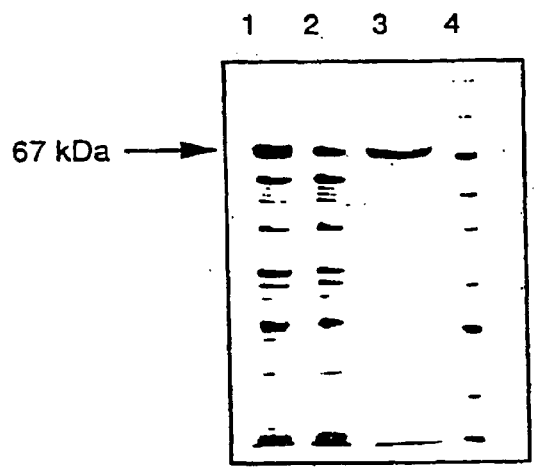
FIGS. 1A–1C: Construction and expression of the Met-GnRH-PE66 chimeric toxin.
Figure 1B:
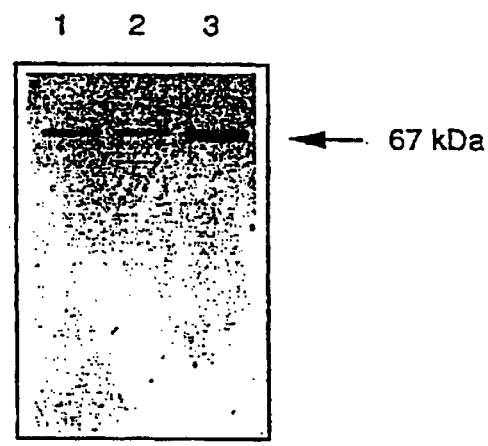
Figure 1C:
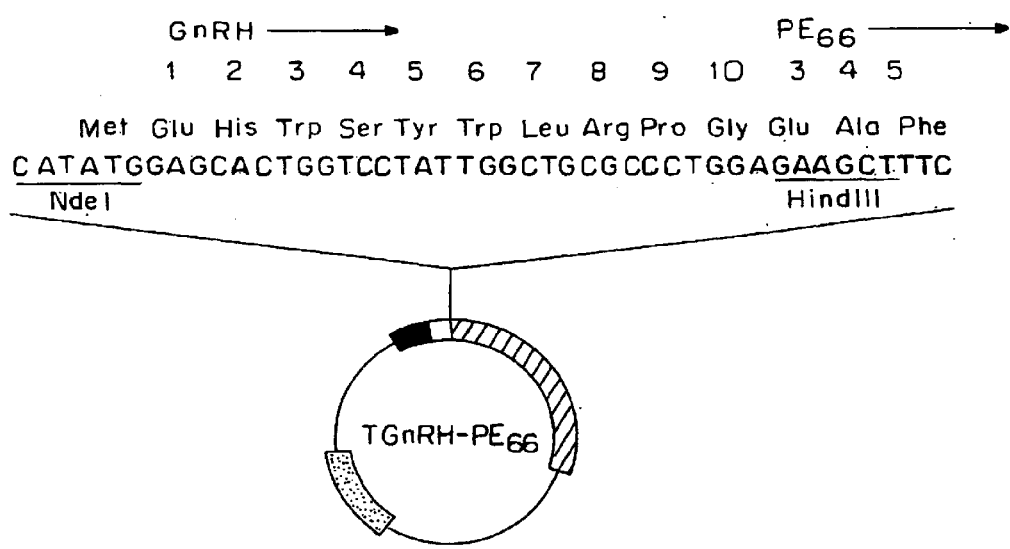

Analysis of the insoluble fraction by SDS/PAGE gel electrophoresis revealed a major band (70%) with an expected molecular mass of 67 kDa, corresponding to the chimeric protein, and two major unrelated bacterial proteins of 42 and 28 kDa (FIG. 1A). Immunoblotting with polyclonal antibodies against PE, confirmed these data (FIG. 1B).

Experiment 4

Effect of the Met-GnRH-PE66 Chimeric Proteins on Various Cell Lines

In the experiments described below, the insoluble fraction of *E. coli* expressing cells was used as the source of the Met-GnRH-PE66 chimeric protein.

The cytotoxic activity of Met-GnRH-PE66 was tested in various established cell lines: SW-48 colon adenocarcinoma, HepG2 hepatocarcinoma, Caco2 colon adenocarcinoma, OVCAR3 ovarian adenocarcinoma, HeLa cervix adenocarcinoma, MDA MB-231 breast adenocarcinoma, HT-29 colon adenocarcinoma. Unless specified, all cell lines were maintained in RPMI 1640 medium, cultured in 100 mm Petri dishes in a humidified atmosphere of 5% CO$_2$/95% air at 37° C. HepG2 and Caco2 were maintained in Eagle's Minimal Essential Medium, and HeLa cells were maintained in Dulbecco's Modified Eagle's Medium. All media were supplemented with 10% fetal calf serum, 2 mM L-glutamine, 100 units/ml of penicillin and 100 μg/ml streptomycin. On day 0, cells (10$^4$ in 0.2 ml culture medium) were seeded in 96 well tissue culture microplates and 24 hours later various concentrations of the Met-GnRH-PE66 were added. After 24 hours incubation [$^3$H]leucine [5 μCi per well] was added for an additional 24 hours. At day 3, the plates were stored at −70° C. for several hours, followed by a quick thawing at 37° C. Cells were harvested on filters and the incorporated radioactivity was measured with a beta counter. The chimeric protein was found to kill cells in a dose-dependent manner, with considerable variation between cell lines (Table 1) ranging from the strong response of HepG2 hepatocarcinoma, SW-48 and Caca2 colon adenocarcinoma (FIG. 2A) to the intermediate one of OVCAR3 ovarian adenocarcinoma, MDA MB-231 breast adenocarcinoma, HT-29 colon adenocarcinoma, and HeLa cervix adenocarcinoma (FIG. 2B). Although cytotoxicity was measured by inhibition of amino acid incorporation, cell death was reflected in cell number and/or cell necrosis 24 hours following the addition of the chimeric protein.

To confirm the specificity of Met-GnRH-PE66 activity, two other PE based recombinant proteins, expressed and extracted under the same conditions, were used as controls. No substantial growth inhibition was exerted by either PE664Glu, encoded by the mutated full length PE gene, or by PIS2, an unrelated 80 bp sequence fused to PE664Glu. When 15 µg/ml of PE664Glu or PIS2 were added, protein synthesis ranged from a slight increase to 20% inhibition in the different cultures. Growth inhibition resulting from treatment with one of the two proteins was considered nonspecific.

The results are expressed as the percent of the control experiments in which cells were not exposed to any protein (results are summarized in Table 1 and in FIG. 2).

TABLE 1

Cytotoxic Activity of Met-GnRH-PE66 on Various Cell Lines

| Cell Line | Origin | $ID_{50}$ (µg Total Protein/Well)* |
|---|---|---|
| Caco2 | Colon adenocarcinoma | 0.4 |
| HT-29 | Colon adenocarcinoma | 1.2 |
| SW-48 | Colon adenocarcinoma | 0.3 |
| OVCAR3 | Ovarian adenocarcinoma | 3 |
| MDA MB-231 | Breast adenocarcinoma | 2.3 |
| HeLa | Cervix adenocarcinoma | 1.8 |
| HepG2 | Hepatocarcinoma | 0.3 |

*The $ID_{50}$ values show the effect of the insoluble fraction enriched with the chimeric protein

Experiment 5

The Effect of Met-GnRH-PE66 on Various Primary Cultures

In order to evaluate the cytotoxic effectiveness of the chimeric proteins on cells resembling the original in vivo tumors as closely as possible and to exclude the possibility that the Met-GnRH-PE66 cytotoxicity was a characteristic developed by cells upon prolonged passages, primary cultures were established.

Fresh tissue specimens were obtained from various cancer patients undergoing therapeutic debulking procedures. Control specimens were obtained from donors or patients undergoing diagnostic or therapeutic procedures for non-malignant diseases. All tissue specimens were washed several times with Leibovitz (L15) medium, and extensively cut with a scalpel. The preparations were then enzymatically proteolysed for 2 hours at 37° C. with gentle shaking in Leibovitz medium containing collagenase type I (200 u/ml), hyaluronidase (100 u/ml), penicillin (1000 units/ml), streptomycin (1 mg/ml), amphotericin B (2.5 µg/ml) and gentamycin (80 µg/ml). Tissue preparations were centrifuged 10 minutes at 200×g and the pellets were suspended in RPMI 1640 medium, supplemented with 10% fetal calf serum, penicillin (100 u/ml) and streptomycin (100 µg/ml) and plated in 100 mm Petri dishes. Cells were grown for one to three weeks to a density of $8 \times 10^6$ cells and histopathological diagnoses and cytotoxic assays were performed. Normal leukocytes from peripheral blood and bone marrow aspirates for cytotoxic assays were obtained by diluting whole blood in one volume of phosphate-buffered saline. The diluted sample was placed over an equal volume of Ficoll-Paque and centrifuged for 10 minutes at 200×g. The cells were resuspended and plated in RPMI 1640 medium containing 20% fetal calf serum, 4 mM 1-glutamine, 50 µM β-mercaptoethanol, non-essential amino acids, 1 mM sodium pyruvate, penicillin (100 units) and streptomycin (100 µg/ml).

The cytotoxic effect of the chimeric protein was variable (Table 2) with up to three-fold differences in $ID_{50}$ observed in colon, breast and ovarian primary cultures originated from different patients (FIGS. 3A, 3C and 3D respectively).

TABLE 2

Cytotoxic Effects of Met-GnRH-PE66 on Various Primary Cultures

| Origin | $ID_{50}$ (µg total protein/well)[a] |
|---|---|
| Colon carcinoma | 0.8–2.5[b] |
| Renal cell carcinoma | 1.2 |
| Breast carcinoma | 1–3[c] |
| Ovarian carcinoma | 1.6–3[d] |
| Bladder Carcinoma | no effect |
| control cells: | |
| Colon | no effect[e] |
| Fibroblasts | no effect[e] |
| Bone marrow | no effect[e] |
| Leukocytes | no effect[e] |

[a]The $ID_{50}$ values show the effect of the insoluble fraction enriched with the chimeric protein
[b]n = 3
[c]n = 4
[d]n = 2
[e]Increasing concentration of Met-GnRH-PE66 did not affect cell growth In cases where metastasis biopsies could also be obtained, cultures of primary tumors alongside with the metastasis were examined for Met-GnPH-PE66 cytotoxicity. The metastatic cells responded in the same manner, and their $ID_{50}$ were even lower than those of the primary tumors. This may be explained by the high homogeneity of the metastasis culture compared with that of the primary culture.

Met-GnRH-PE66 was also tested on cultures of benign colon peripheral blood bone marrow and skin fibroblasts from healthy donors. The addition of up to 15 µg/ml of the chimeric protein did not result in any measurable dose dependent killing (FIG. 3F).

Experiment 6

Histopathological Diagnosis of Primary Cultures

One of the basic questions regarding the veracity of the primary culture assays is of the epithelial origin of the cells. The tendency of cells in primary culture to lose their epithelial morphology has been described in several carcinomas. To confirm the absence of any substantial amount of "contaminating" fibroblasts, differential staining was performed.

Cells were stained as follows: 10,000 cells were plated on a microscope slide using a cytospin, followed by several minutes incubation at room temperature. Dried slides were fixed by soaking in −20° C. cold methanol for 15 minutes and in −20° C. cold acetone for a few seconds. Slides were kept at −20° C. until staining. Staining was carried out with anti-desmin and anti-keratin antibodies to distinguish fibroblast from epithelial cells, respectively. This staining indicated that the vast majority of the cells (80–100%) were indeed epithelial, even in cases where the cultures exhibited a fibroblast-like shape (FIGS. 4A and 4B).

Further confirmation was achieved by staining with specific antitumor marker antigens according to the type of cancer. Formalin fixed sections from the original tumors and the primary cultures cells displayed the same pattern and intensity of staining.

Experiment 7

Specific Binding by Met-GnRH-PE66

To support the findings that colon adenocarcinoma cell lines and primary cultures can be targeted and killed by Met-GnRH-PE66, the ability of plasma membrane fractions from a colon adenocarcinoma cell line to specifically bind GnRH, was examined. The addition of increasing concentrations of Met-GnRH-PE66 chimeric toxin resulted in dose-related displacement of the $^{125}$I-GnRH bound to these membranes. A semiconfluent 100 mm dish of the SW-48 colon adenocarcinoma cell line was washed and the cells were scraped off the plate with a rubber policeman. The collected cells were homogenized in ice-cold assay buffer (10 mM Tris HCl, pH 7.6, 1 mM dithiothreitol, 0.15% bovine serum albumin, 1 mM EDTA) and centrifuged at 250×g for 15 minutes (4° C.). The resulting pellet was discarded and the supernatant was centrifuged at 20,000×g for 30 minutes (4° C.). The plasma membrane pellet was resuspended in cold assay buffer. Aliquots containing 70 $\mu$g plasma membrane protein in a final volume of 100 $\mu$l, were incubated for 2 hours on ice with $6 \times 10^{-6}$ M (240,000 cpm) $^{125}$I-GnRH either in the presents or absence of ($10^{-4}$–$10^{-10}$ M) unlabeled GnRH authentic peptide and analog (des-Gly, [d-Ala]-LHRH) or ($2.5 \times 10^{-5}$–$10^{-9}$ M) Met-GnRH-PE66 chimeric toxin. Following incubation, samples were washed through Whatman GF/C filters with 10 ml of cold assay buffer and counted in a gamma counter.

The addition of increasing concentrations of Met-GnRH-PE66 chimeric toxin resulted in dose related displacement of the $^{125}$I-GnRH bound to these membranes. Unlabeled authentic GnRH peptide and the analogue des-Gly10 [D-Ala6]-LHRH produced similar results. As can be seen in FIG. 5, binding of the labeled GnRH to SW-48 colon adenocarcinoma cell line was specific and displacement by the Met-GnRH-PE66 chimeric toxin was as efficient as that by the GnRH analogue peptide. There was 37% non-specific binding.

Experiment 8

Met-GnRH-PE40 and Met-GnRH-PE66 Purification

The pellet of the insoluble fraction was suspended and stirred on ice in denaturation buffer (6 M guanidium HCl, 0.1 M Tris HCl , pH 8.6, 1 mM EDTA, 0.05M NaCl and 10 mM DDT). After an additional centrifugation, the reduced and denatured protein was diluted 1:100 in refolding buffer (50 mM Tris HCl , pH 8, 1 mM EDTA, 0.25M NaCl, 0.25 M L-arginine and 5 mM DTT) and kept at 4° C. for 48 hours. Refolded protein solutions were diluted to 8 mM in TE20 buffer (20 mM Tris, pH 8.0, 1 mM EDTA). DEAE Sepharose was added and stirred for half an hour at 4° C. before being packed onto a column. Washing of the column was done with 80 mM NaCl, in TE20 buffer for Met-GnRH-PE66 and 50 mM NaCl in TE20buffer for Met-GnRH-PE40. Elution was performed with the linear gradient of 2×200 ml of 0.08–0.35 M NaCl, in TE20 (20 mM Tris, ph 8.0, 1 mM EDTA) buffer. The peak fractions were pooled, 0.5M L-arginine was added and stirred cell was used for concentration. 3 ml of the pooled fractions from the ion exchange column were loaded onto a Sepharyl S-200 HR gel filtration column, in 0.5 M NaCl, 0.15 M K-phosphate buffer, pH 6.0. The peak fractions were pooled, dialyzed against phosphate saline buffer and kept in aliquots at −20° C. Purification of Met-GnRH-PE66 and Met-GnRH-PE40 is demonstrated in FIGS. 6 and 7, respectively.

Experiment 9

Effect of Highly-Purified Met-GnRH-PE Chimeric Proteins on SW-48 Colon Adenocarcinoma Cell Line The cytotoxic activity of the purified Met-GnRH-PE66 and Met-GnRH-PE40 on the SW-48 colon adenocarcinoma cell line measuring the inhibition of protein synthesis. The chimeric proteins were found to kill cells in a dose dependent manner. The $ID_{50}$ of the purified Met-GnRH-PE66 chimeric toxin was two to three times lower than the refolded insoluble fraction. The $ID_{50}$ of the Met-GnRH-PE40 purified protein was three to four times lower than the purified Met-GnRH-PE66 (FIG. 8).

What is claimed is:

1. A method for the treatment of adenocarcinoma or hepatocarcinoma in a mammal, comprising administering to the body of a mammal in need of such therapy an effective amount, sufficient to at least reduce the growth of said adenocarcinoma or hepatocarcinoma, of at least one fused chimeric protein comprising a linear genetically engineered molecule consisting essentially of peptide bonds, produced by fusing, at the level of cDNA:

A. DNA encoding at least one cell targeting moiety consisting essentially of Met-GnRH or a Met-GnRH analog that specifically binds to GnRH binding sites on Caco2 adenocarcinoma cells; and B. DNA encoding at least one cell killing moiety.

2. A method according to claim 1, wherein said fused chimeric protein is produced by fusing at the cDNA level an oligonucleotide encoding gonadotropin releasing hormone (GnRH) or a GnRH analog, preceded by a Met, to a mutated DNA fragment of the full length *Pseudomonas* exotoxin (PE), encoding the protein Met-GnRH-PE66.

3. A method according to claim 1, wherein said fused chimeric protein produced by fusing at the cDNA level an oligonucleotide encoding gonadotropin releasing hormone (GnRH) or a GnRH analog, preceded by a Met, to a DNA fragment comprising domains II and III of the *Pseudomonas* exotoxin (PE), encoding the protein Met-GnRH-PE40.

4. A method for adenocarcinoma or hepatocarcinoma therapy according to claim 1, wherein said administering step is by systemic administration of said chimeric protein.

5. A method of treating a mammal having at least one adenocarcinoma or hepatocarcinoma, comprising administering to said mammal in need thereof, an amount sufficient to ameliorate the effects of said adenocarcinoma or hepatocarcinoma, of a pharmaceutical composition, comprising a fused chimeric protein comprising a linear genetically engineered molecule consisting essentially of peptide bonds, produced by fusing, at the level of cDNA:

A. DNA encoding at least one cell targeting moiety consisting essentially of Met-GnRH or a Met-GnRH analog that specifically binds to GnRH binding sites on Caco2 adenocarcinoma cells; and B. DNA encoding at least one cell killing moiety.

6. A method of treating a mammal having endometriosis, comprising administering to said mammal in need thereof, an amount sufficient to ameliorate the effects of said endometriosis, of a pharmaceutical composition, comprising a fused chimeric protein comprising a linear genetically engineered molecule consisting essentially of peptide bonds, produced by fusing, at the level of cDNA:

A. DNA encoding at least one cell targeting moiety consisting essentially of Met-GnRH or a Met-GnRH analog that specifically binds to GnRH binding sites on Caco2 adenocarcinoma cells; and B. DNA encoding at least one cell killing moiety.

7. A method for endometrioma therapy according to claim 6, further comprising trans-cervical washing of the mammal's endometrial cavity.

8. A method of treating a mammal having a uterine myoma, comprising administering to said mammal in need thereof, an amount sufficient to ameliorate the effects of said uterine myoma, of a pharmaceutical composition, comprising a fused chimeric protein comprising a linear genetically engineered molecule consisting essentially of peptide bonds, produced by fusing, at the level of cDNA:
- A. DNA encoding at least one cell targeting moiety consisting essentially of Met-GnRH or a Met-GnRH analog that specifically binds to GnRH binding sites on Caco2 adenocarcinoma cells; and
- B. DNA encoding at least one cell killing moiety.

9. A method of treating a mammal having a pituitary adenoma, comprising administering to said mammal in need thereof, an amount sufficient to ameliorate the effects of said pituitary adenoma, of a pharmaceutical composition, comprising a fused chimeric protein comprising a linear genetically engineered molecule consisting essentially of peptide bonds, produced by fusing, at the level of cDNA:
- A. DNA encoding at least one cell targeting moiety consisting essentially of Met-GnRH or a Met-GnRH analog that specifically binds to GnRH binding sites on Caco2 adenocarcinoma cells; and
- B. DNA encoding at least one cell killing moiety.

10. A method of treating a mammal having BPH, comprising administering to said mammal in need thereof, an amount sufficient to ameliorate the effects of said BPH, of a pharmaceutical composition, comprising a fused chimeric protein comprising a linear genetically engineered molecule consisting essentially of peptide bonds, produced by fusing, at the level of CDNA:
- A. DNA encoding at least one cell targeting moiety consisting essentially of Met-GnRH or a Met-GnRH analog that specifically binds to GnRH binding sites on Caco2 adenocarcinoma cells; and
- B. DNA encoding at least one cell killing moiety.

11. A method of treating a mammal having polycystic breast disease, comprising administering to said mammal in need thereof, an amount sufficient to ameliorate the effects of said polycystic breast disease, of a pharmaceutical composition comprising a fused chimeric protein comprising a linear genetically engineered molecule consisting essentially of peptide bonds, produced by fusing, at the level of cDNA:
- A. DNA encoding at least one cell targeting moiety consisting essentially of Met-GnRH or a Met-GnRH analog that specifically binds to GnRH binding sites on Caco2 adenocarcinoma cells; and
- B. DNA encoding at least one cell killing moiety.

12. A method according to claim 5, wherein said fused chimeric protein is produced by fusing at the cDNA level an oligonucleotide encoding gonadotropin releasing hormone (GnRH) or a GnRH analog, preceded by a Met, to a mutated DNA fragment of the full length *Pseudomonas* exotoxin (PE), encoding the protein Met-GnRH-PE66.

13. A method according to claim 5, wherein said fused chimeric protein is produced by fusing at the cDNA level an oligonucleotide encoding gonadotropin releasing hormone (GnRH) or a GnRH analog, preceded by a Met, to a DNA fragment comprising domains II and III of the *Pseudomonas* exotoxin (PE), encoding the protein Met-GnRH-PE40.

14. A method according to claim 6, wherein said fused chimeric protein is produced by fusing at the cDNA level an oligonucleotide encoding gonadotropin releasing hormone (GnRH) or a GnRH analog, preceded by a Met, to a mutated DNA fragment of the full length *Pseudomonas* exotoxin (PE), encoding the protein Met-GnRH-PE66.

15. A method according to claim 6, wherein said fused chimeric protein is produced by fusing at the cDNA level an oligonucleotide encoding gonadotropin releasing hormone (GnRH) or a GnRH analog, preceded by a Met, to a DNA fragment comprising domains II and III of the *Pseudomonas* exotoxin (PE), encoding the protein Met-GnRH-PE40.

16. A method according to claim 8, wherein said fused chimeric protein is produced by fusing at the cDNA level an oligonucleotide encoding gonadotropin releasing hormone (GnRH) or a GnRH analog, preceded by a Met, to a mutated DNA fragment of the full length *Pseudomonas* exotoxin (PE), encoding the protein Met-GnRH-PE66.

17. A method according to claim 8, wherein said fused chimeric protein is produced by fusing at the cDNA level an oligonucleotide encoding gonadotropin releasing hormone (GnRH) or a GnRH analog, preceded by a Met, to a DNA fragment comprising domains II and III of the *Pseudomonas* exotoxin (PE), encoding the protein Met-GnRH-PE40.

18. A method according to claim 9, wherein said fused chimeric protein is produced by fusing at the cDNA level an oligonucleotide encoding gonadotropin releasing hormone (GnRH) or a GnRH analog, preceded by a Met, to a mutated DNA fragment of the full length *Pseudomonas* exotoxin (PE), encoding the protein Met-GnRH-PE66.

19. A method according to claim 9, wherein said fused chimeric protein is produced by fusing at the cDNA level an oligonucleotide encoding gonadotropin releasing hormone (GnRH) or a GnRH analog, preceded by a Met, to a DNA fragment comprising domains II and III of the *Pseudomonas* exotoxin (PE), encoding the protein Met-GnRH-PE40.

20. A method according to claim 10, wherein said fused chimeric protein is produced by fusing at the cDNA level an oligonucleotide encoding gonadotropin releasing hormone (GnRH) or a GnRH analog, preceded by a Met, to a mutated DNA fragment of the full length *Pseudomonas* exotoxin (PE), encoding the protein Met-GnRH-PE66.

21. A method according to claim 10, wherein said fused chimeric protein is produced by fusing at the cDNA level an oligonucleotide encoding gonadotropin releasing hormone (GnRH) or a GnRH analog, preceded by a Met, to a DNA fragment comprising domains II and III of the *Pseudomonas* exotoxin (PE), encoding the protein Met-GnRH-PE40.

22. A method according to claim 11, wherein said fused chimeric protein is produced by fusing at the CDNA level an oligonucleotide encoding gonadotropin releasing hormone (GnRH) or a GnRH analog, preceded by a Met, to a mutated DNA fragment of the full length *Pseudomonas* exotoxin (PE), encoding the protein Met-GnRH-PE66.

23. A method according to claim 11, wherein said fused chimeric protein is produced by fusing at the cDNA level an oligonucleotide encoding gonadotropin releasing hormone (GnRH) or a GNRH analog, preceded by a Met, to a DNA fragment comprising domains II and III of the *Pseudomonas* exotoxins (PE), encoding the protein Met-GnRH-PE40.

* * * * *